(12) United States Patent
Menn et al.

(10) Patent No.: US 11,051,852 B2
(45) Date of Patent: Jul. 6, 2021

(54) FIXTURING DEVICE FOR MEDICAL INSTRUMENTS

(71) Applicants: Dmitri Menn, Marblehead, MA (US); Michael Golinder, Encino, CA (US)

(72) Inventors: Dmitri Menn, Marblehead, MA (US); Michael Golinder, Encino, CA (US)

( * ) Notice: Subject to any disclaimer, the term of this patent is extended or adjusted under 35 U.S.C. 154(b) by 107 days.

(21) Appl. No.: 16/398,502

(22) Filed: Apr. 30, 2019

(65) Prior Publication Data

US 2019/0336168 A1 Nov. 7, 2019

Related U.S. Application Data

(60) Provisional application No. 62/665,988, filed on May 2, 2018.

(51) Int. Cl.
*A61B 17/42* (2006.01)
*F16B 2/06* (2006.01)
*A61B 17/00* (2006.01)

(52) U.S. Cl.
CPC ............ *A61B 17/4241* (2013.01); *F16B 2/06* (2013.01); *A61B 2017/00477* (2013.01)

(58) Field of Classification Search
CPC ...... A61B 17/4241; A61B 2017/00477; A61B 2017/00292; A61M 39/285; A61M 2039/087

USPC ......................................................... 604/250
See application file for complete search history.

(56) References Cited

U.S. PATENT DOCUMENTS

| | | | |
|---|---|---|---|
| 6,530,880 B2* | 3/2003 | Pagliuca | A61B 1/00154 600/102 |
| 6,821,243 B2* | 11/2004 | Pagliuca | A61B 90/50 600/102 |
| 10,549,071 B2* | 2/2020 | Falb | A61M 39/06 |
| 10,687,906 B2* | 6/2020 | Grover | A61B 17/34 |
| 2010/0168682 A1* | 7/2010 | Braga | A61M 39/284 604/250 |
| 2020/0324084 A1* | 10/2020 | Falb | A61M 25/0113 |

* cited by examiner

*Primary Examiner* — Bradley Duckworth

(57) ABSTRACT

A connection device attached to one structure includes structures having adjacent slots that are alligned to receive and permit placement of an elongated member, and are subsequently relatively movable to retain the elongated member to restrict or occlude the adjacent slot opening restricting removal, and further provides a sheer force between the structures each having the slot to receive the elongated member, to engage and secure the outer surface of a tubular member received into an aperture common through 2 adjacent members, each member aperture having an axis parallel to and offset from the other, wherein rotation of one of the 2 members causes the surface of the offset aperture and the surface of the non-offset aperture to apply a shear force and/or friction to engage and retain the tubular member. Access to the aperture is provided by slot extending from the aperture to the member periphery.

17 Claims, 4 Drawing Sheets

FIXTURING DEVICE FOR MEDICAL INSTRUMENTS

FIELD OF THE INVENTION

The invention relates to the connection devices for applications that require fixturing in an instrument, a tubular or elongated member or shaft in a certain position and more specifically an adapter for securing Uterine Manipulator (UM) or other medical element to a Uterine Positional System (UPS) or other related medical device.

BACKGROUND OF THE INVENTION

During many GYN/Laparoscopic surgical, or similarly other medical procedures, surgeons use a particular device having a narrow diameter such as a Uterine Manipulator (UM) that allows them to hold uterus in a fixed position and/or move it so that laparoscopic instruments would have the needed access to the certain operating area. Securing a UM requires an unobtrusive device that can have a firm grip on the small diameter UM shaft and that can be attached to UPS, and can be easily and quickly used without causing disruption to ongoing operation or other delicate proceedure, and provide a simple, sure and rapid connection and disconnection. Similar problems of securing a narrow and/or tubular device may exist for other medical and non-medical proceedures.

SUMMARY

The connection device according to the present invention attached to one structure includes structures having adjacent slots that are alligned to receive and permit placement of an elongated member, and are subsequently relatively movable to retain the elongated member to restrict or occlude the adjacent slot opening restricting removal, and further provides a sheer force between the structures each having the slot to receive the elongated member, to engage and secure the outer surface of a tubular member received into an aperture common through 2 members, each member aperture having an axis parallel to and offset from the other, wherein rotation of one of the 2 members causes the surface of the offset aperture and the surface of the non-offset aperture to apply a shear force and/or friction to engage and retain the tubular member. Access to the aperture is provided by slot extending from the aperture to the member periphery, through which the tubular member may be inserted into the connection device and further into attached equipment.

BRIEF DESCRIPTION OF THE DRAWING

These and further features according to the present invention will be better understood by reading the following Detailed Description together with the Drawing figures, wherein.

DETAILED DESCRIPTION

Figure 1:
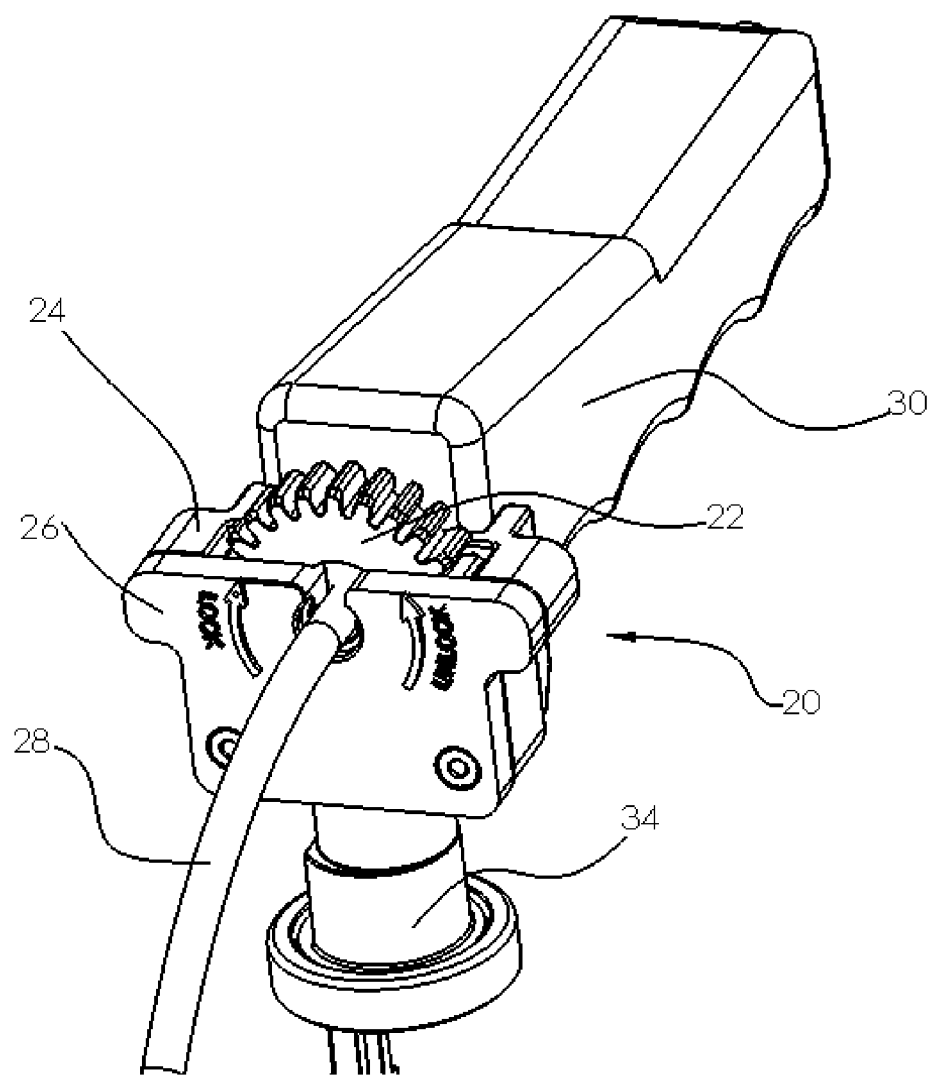
FIG. 1 shows a perspective view of one embodiment of the present invention applied to a Uterine Manipulator and the Adapter Lock assembly attached to it with the locking member in the vertical position so that the shaft (of the Uterine Manipulator) could be inserted in it.

Typically, as shown in FIG. 1, a tubular member 28 will be joined and secured to a structure 30 with the adaptor lock 20 that provides restricted tubular member motion in the direction of the tubular member 28 axis and rotationally about that axis, preventing tubular member rotation or axial movement relative to the attached structure 30, which in the embodiment shown, is the handle of the UM. The clamping device of the present invention comprises one or more slotted base members 24, 26 and an intervening slotted clamping member 22 which are sequentially disposed along the axis of the tubular member to be clamped.

Figure 2:
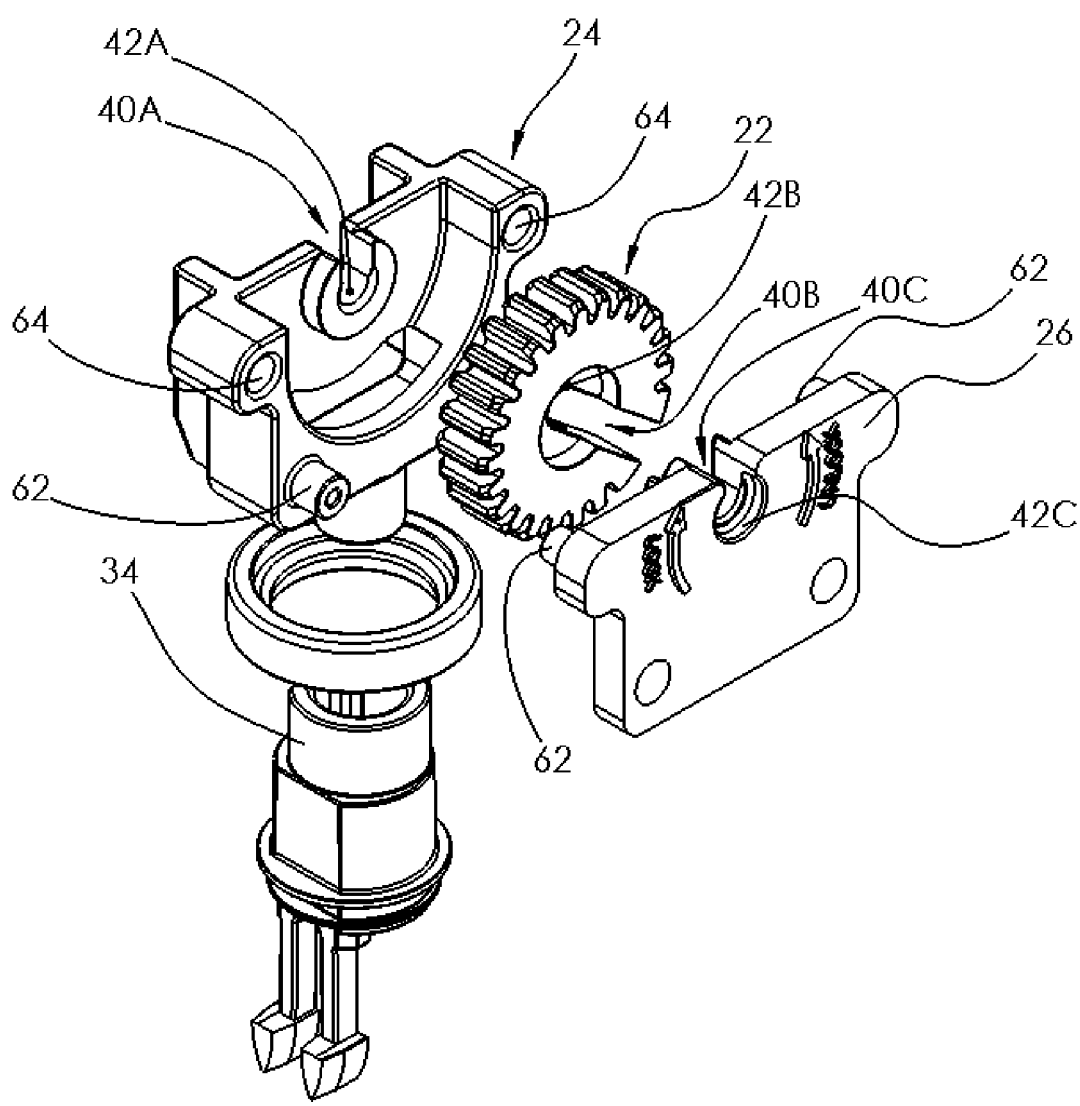
FIG. 2 shows an exploded, persective view of the Adapter Lock assembly of FIG. 1 with the wheel in the rotated position so that the shaft of the UM could be retained therein.

As more clearly seen in the exploded view of FIG. 2, each member 22, 24, and 26 are complementary and typically have confronting planar surface portions, and include a slot (e.g. 40A, 40B, 40C) width that is sufficient, when the slots are alligned, to allow passage of the tubular member therethrough until it reaches a slot interior end of the base member(s) and clamping member, and each interior end typically comprises a cylindrical (or curved or non-linear or otherwise shaped to engage a portion of the out surface of tubular member 28) surface 42A, 42B, 42C against which the tubular member 28 is seated. After the tubular member 28 is placed within the slots 40A, 40B 40C against the cylindrical surfaces 42A, 42B, 42C, it may be further advanced into and rotationally oriented to connected operational structure 30 associated with the tubular member apparatus application. In the embodiment 20 of FIG. 1, the adaptor lock 20 non-rotating base member 24 is secured to the structure 30.

The base members 24, 26 cylindrical surfaces 42A and 42C have substantially the same surface locus and center axis, such that when the slots 40A, 40B, 40C are aligned, clamping member cylindrical surface surface 42B also has a surface locus alligned to be substantially the same as the base member 24, 26 cylindrical surface 42A, 42C locus, preferably (but not necessarily) forming a substantially common surface engaging the received tubular member 28. After the exemplary tubular member 28 is seated in the base and clamping members 22, 24, 26 and slot terminal cylindrical surfaces, the clamping member 22 and corresponding cylindrical surface 42B is rotatable relative to the base members 24, 26 to cause the slot 40B of clamping member 22 to be at a different position relative to slots 40A, 40C to interfere and restrict the tubular member 28 to be withdrawn via slots 40A, 40B, and 40C. Simultaneously, this rotation of clamping member 22 about an axis (52, FIG. 3) offset from the axis 54 of the base member 24, 26 cylindrical surfaces 42A, 42C, and appear, relative to base member cylindrical surfaces 42A, 42C to be moving eccentrically about the base member cylindrical surfaces common axis. However, in so doing, clamping member 22 cylindrical surface 42B imparts a shear force on the tubular member 28 against adjoining base member cylindrical surfaces 42A, 42C.

Figure 3:
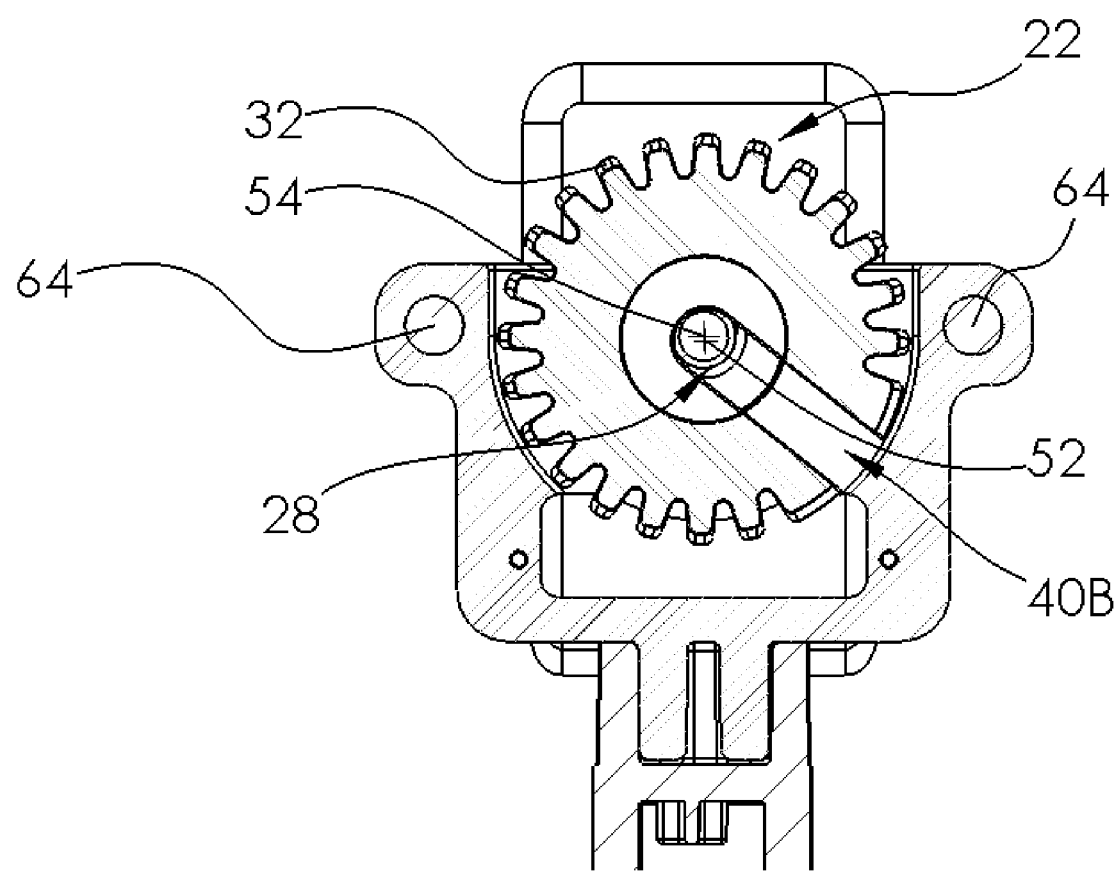
FIG. 3 shows a front elevation cross-section view of one of the embodiments of the device showing an axis of the base member cylindrial surface and the offset axis of the clamping member, and clamping member drive teeth.

The slots 42A and 42C of the base members 24 and 26 are shown as alligned (but unlabeled) in FIG. 1, permitting the tubular member 28 to enter the alligned slots and fully seat on the cylindrical surfaces 42A, 42B, 42C of FIG. 2 (but with clamping member 22 shown rotated relative base members 24 and 26), but unclamped thereto. However, the clamping member 22 is shown in FIG. 3 as having been rotated on its axis 53 more than 90 degrees from the alligned-slot position shown in FIG. 1, which axis 54 differes from the axis 52 of the base members 24 and 26 cylindrical surface by an amount sufficient to secure the received tubular member as desired. Typically, rotation of the clamping member 22 relative to the base member(s) 24, 26 are on parallel axes each aligned with a corresponding surface 42A, 42B, and 42C radius. The amount of axis 52 offset is also determined by the deformation and/or reslience qualities of the tubular member 28, in FIG. 3. Moreover, clamping member 22 slot 40B is offset from slots 40A, 40C, inhibiting removal of tubular member 28 through the slots 40A, 40B, 40C.

The profiles of either or any of the cylindrical surfaces 42A, 42B, 42C may be other than cylindrical sections as chosen complement or engage (e.g. non-linear or abrasive to) the tubing member 22 outer surface to enhance tubular member retention and/or reduction of deformation within the embodiment 20. Also, alternate embodiments having a minimum of one base member and one clamping member, or more base and/or clamping members, than shown, but configured to conform to the requirements listed herein. Furthermore, there may be embodiments wherein both the base and clamping members move relative to each other to provide the desired clamping.

The clamping member 22 in the embodiment 20 comprises a gear-like structure, having teeth 32 driven by hand on an outward extending mounting adapter 34 that attaches the adapter lock embodiment 20 to the UPS or other related structure. The clamping member 22 is rotated by hand relative to the base members 24, 26, and therefore clamping of the tubing member 28. In the embodiment shown, the outer (peripheral edge) surface of the clamping member 22 has a variegated (gear-like 32, here) contour that facilitates hand engagement.

Figure 4:
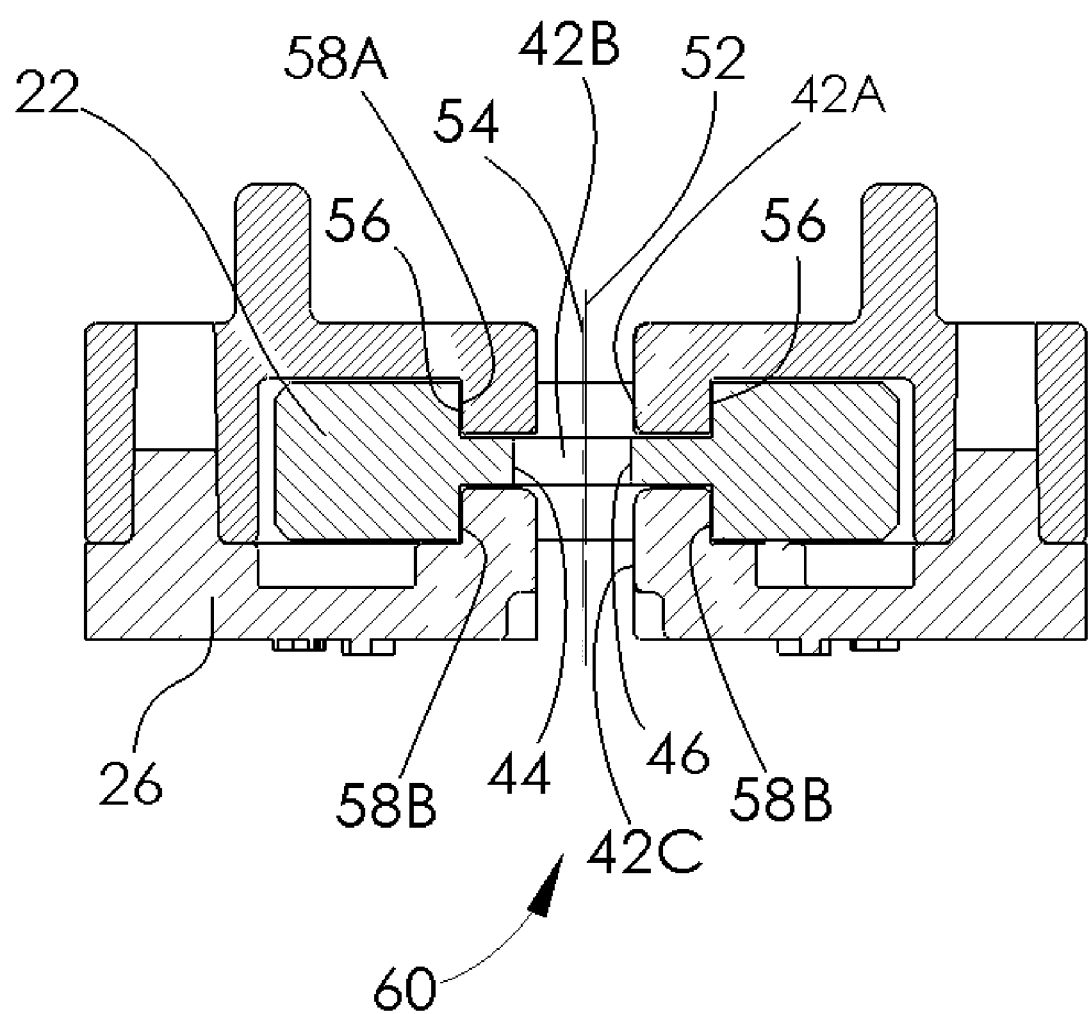
FIG. 4 shows a plan view cross section of one embodiment including the base members and clamping member in slight rotation relative to the base members.

A horizontal cross-section 60 of the embodiment in plan view is shown in FIG. 4, wherein the clamping member 22 is rotated slightly, revealing a cylindrical surface 42B showing expansion of the surface 44 distance due to the contribution of the slot 40B and offset surface 42B relative, while the opposing side has an incursion 46 which applies compression and/or a shear force on the tubing member (not shown in FIG. 4).

In the exemplary embodiment 20 shown, the clamping member has a larger thickness distal from its center and has an annular surfaces 56 that confronts and engages a confronting mating annular surfaces 58A, 58B on members 24 and 26 to form bearing to support the clamping member and permit rotation relative the members 24 and 26 as previously described The clamping member 22 also acts as a cover and has a enclosing cylindrical bearing surfaces 56 that is coaxial with the basemember bearing surfaces 58A, 59B. The cover base member 26 and base member 24 also have four features 62 near the base member corners, received by mating apertures 64, connecting it firmly to the base 24 and forms a housing for clamping member 22.

Thus, the apparatus according to the present invention provides a complete, sure, quick and easily adjusted clamping device. Further modifications and substitutions by one of ordinary skill in the art are within the scope of the present invention, which is not to be limited, except by the claims that follow.

What is claimed is:

1. A rotary clamping apparatus for retaining a tubular member having an outer circumference, comprising:

a first member having a planar surface and a slot therein having a depth extending from a periphery of said first member to an interior region and a length extending substantially perpendicular to said depth, said first member slot being shaped to receive therein and engage said tubular member outer circumference at a first member first location and formed to substantially center said tubular member within and retain said tubular member parallel to said first member slot length; and a second member having a planar surface disposed to confront said first member planar surface, and including a slot therein having a depth extending from a periphery thereof to an interior region and a length extending substantially perpendicular to said depth, said second member slot being shaped to receive therein and engage said tubular member outer circumference at a second member first location and formed to substantially center said tubular member therein and retain said tubular member parallel to said second member slot, said second member planar surface and second member first location, and said first member planar surface and first member first location being alligned to simultaneously receive said tubular member therein, wherein said second member is rotatable relative to said first member to permit insertion of said tubular member into said second member slot and into said first member slot to said first member first location simultaneously, and said second member is rotatable about said first location relative to said first member to inhibit removal of said tubular member from said second member slot wherein said first member slot includes a nonlinear portion shaped to have a first axis and a first radius and engage a portion of the outer surface of said tubular member, said second member slot includes a nonlinear portion movable about a second member axis and shaped to have a second radius and engage a portion of the outer surface of said tubular member, and upon rotation about said second member axis relative to said first member slot location, generate a shear force across said tubular member between said first member slot nonlinear portion and said second member slot nonlinear portion, and said first member slot nonlinear portion first radius and said second member slot nonlinear portion second radius upon said rotation are offset relative to each other.

2. The rotary clamping apparatus of claim 1, wherein said first member slot and said second member slots are aligned to simultaneously receive said tubular member therein, and said second member slot is movable about said second member axis to interfere with removing said tubular member from said first member slot and said second member slot.

3. The rotary clamping apparatus of claim 1, wherein said first member slot nonlinear portion include a curved first member slot end portion and said second member slot nonlinear portion include a curved second member slot end portion eccentrically movable relative to said curved first member slot end portion.

4. The rotary clamping apparatus of claim 1, wherein rotation of said second member relative to said first member is on said second axis in parallel disposition with respect to said first axis.

5. The rotary clamping apparatus of claim 1, wherein said first member forms a housing retaining said second member therein.

6. The rotary clamping apparatus of claim 1, wherein said first member includes a bearing surface and said second member includes a bearing surface complementary to said first member bearing surface and disposed to engage each other.

7. The rotary clamping apparatus of claim 1, wherein said second member includes a varigated gripping surface.

8. A tubing clamp, comprising:

a first clamp member having a slot extending to an end in the interior of said first clamp member and having an end surface including an axis and shaped to receive a section of tubing at said first clamp member end surface axis;

a second clamp member disposed to confront and rotate relative to said first clamp member, and having a slot extending to an end in the interior of said second clamp member and having an end surface including an axis and shaped to receive a section of tubing at said second clamp member end surface axis parallel to and offset from said first clamp member end surface axis providing a selective alignment of said first clamp member end surface and said second clamp member end surface, wherein said first clamp member slot and said second clamp member slot are disposed to receive a tubing section therein and at said first clamp member end surface and said second clamp member end surface, and said first clamp member and said second clamp member engage and retain said tubing section at said first clamp member end surface and said second clamp member end surface when one of said first clamp member and said second clamp member is rotated about its corresponding first clamp member end surface axis and said second clamp member end surface axis.

9. The tubing clamp of claim 8, wherein said first clamp member slot and said second clamp member slot are aligned to simultaneously receive said section of tubing therein, and said second clamp member slot is movable about said second member end surface axis to interfere with removing said section of tubing from said first clamp member slot and said second clamp member slot.

10. The tubing clamp of claim 8, wherein said first clamp member slot includes a nonlinear portion shaped to engage a portion of the outer surface of said section of tubing at a slot location and said second clamp member slot includes a nonlinear portion movable about a second clamp member end surface axis and shaped to engage a portion of the outer surface of said section of tubing, and upon rotation about said second clamp member end surface axis relative to said first clamp member slot location, generate a shear force across said section of tubing between said first member slot nonlinear portion and said second member slot nonlinear portion.

11. The tubing clamp of claim 10, wherein said first member slot nonlinear portion includes a curved first end portion and said second member slot nonlinear portion includes a curved second end portion.

12. The tubing clamp of claim 10, wherein said first member slot nonlinear portion and said second member slot nonlinear portion each comprise a surface having a corresponding one of a first radius and a second radius.

13. The tubing clamp of claim 12, wherein said first member slot nonlinear portion radius and said second member slot nonlinear portion radius are offset relative to each other.

14. The tubing clamp of claim 12, wherein said first member slot nonlinear portion radius and said second member slot nonlinear portion radius are parallel.

15. The tubing clamp of claim 12, wherein said first member and said second member each include a planar surface in confronting disposition.

16. The tubing clamp of claim 8, wherein said first member forms a housing retaining said second member therein.

17. The tubing clamp of claim 16, wherein said first member includes a bearing surface and said second member includes a bearing surface complementary to said first member bearing surface and disposed to retain said first member.

\* \* \* \* \*